United States Patent [19]

Cormier et al.

[11] Patent Number: 4,627,893
[45] Date of Patent: Dec. 9, 1986

[54] MEANS AND METHODS FOR QUANTITATIVE DETERMINATION OF ANALYTE IN LIQUIDS

[75] Inventors: Alan D. Cormier, Newburyport, Mass.; Melvin S. Weinberg, Nashua, N.H.

[73] Assignee: AMDEV, Inc., Danvers, Mass.

[21] Appl. No.: 594,246

[22] Filed: Mar. 28, 1984

[51] Int. Cl.⁴ .................... G01N 27/30; G01N 27/38
[52] U.S. Cl. ........................ 204/1 T; 73/1 R; 204/401; 204/402; 204/409; 204/411; 204/414
[58] Field of Search ............... 204/409, 414, 411, 412, 204/401, 402, 403, 1 T; 73/1 R

[56] References Cited

U.S. PATENT DOCUMENTS

| | | | |
|---|---|---|---|
| 3,505,196 | 4/1970 | Dahms | 204/195 |
| 3,648,159 | 3/1972 | Stansell et al. | 324/30 |
| 3,840,438 | 10/1974 | Ast et al. | 204/1 |
| 3,874,850 | 4/1975 | Sorensen et al. | 23/230 |
| 3,884,640 | 5/1975 | Lock et al. | 23/253 |
| 3,926,765 | 12/1975 | Haddad | 204/435 X |
| 3,957,607 | 5/1976 | Simon et al. | 204/180 |
| 3,963,440 | 6/1976 | Stein et al. | 23/253 |
| 3,966,413 | 6/1976 | Marinenko | 204/411 |
| 3,997,420 | 12/1976 | Buzza | 204/411 |
| 4,105,509 | 8/1978 | Jungck | 204/1 T |
| 4,160,714 | 7/1979 | Andersen et al. | 204/195 |
| 4,206,027 | 6/1980 | Schindler et al. | 204/411 |
| 4,207,394 | 6/1980 | Aldridge et al. | 435/34 |
| 4,221,567 | 9/1980 | Clark et al. | 23/230 |
| 4,282,081 | 8/1981 | Arrance | 204/414 X |
| 4,283,262 | 8/1981 | Cormier et al. | 204/195 |
| 4,361,539 | 11/1982 | Weinberg et al. | 422/68 |
| 4,361,540 | 11/1982 | Weinberg et al. | 422/68 |
| 4,366,038 | 12/1982 | Kearney et al. | 204/195 |
| 4,399,362 | 8/1983 | Cormier et al. | 250/430 |
| 4,410,631 | 10/1983 | Czaban et al. | 436/8 |
| 4,443,407 | 4/1984 | Weinberg et al. | 422/68 |
| 4,490,236 | 12/1984 | Petty | 204/409 |

FOREIGN PATENT DOCUMENTS

| | | | |
|---|---|---|---|
| 2854444 | 7/1979 | Fed. Rep. of Germany | 204/412 |
| 2025629 | 1/1980 | United Kingdom | 27/40 |

Primary Examiner—G. L. Kaplan
Attorney, Agent, or Firm—Wolf, Greenfield & Sacks

[57] ABSTRACT

A testing module is provided having units which can be arranged seriatim to provide narrow through passageways linked to each other for quantitative determination of analytes passing through the units as by electrical testing with electrodes. Auxiliary passageways are preferably used in one unit to allow flushing of a first sample chamber without contamination from a second sample chamber. An electrode holder carries a membrane backed by a gel to aid in electrically linking the membrane to an electrode and to support the membrane in a substantially planar condition in use.

19 Claims, 12 Drawing Figures

MEANS AND METHODS FOR QUANTITATIVE DETERMINATION OF ANALYTE IN LIQUIDS

BACKGROUND OF THE INVENTION

A large number of measuring chamber units have been used in the past in various electrochemical measuring apparatus. U.S. Pat. No. 4,160,714 describes a single unit measuring chamber used for pH values, gas values and other types are known for use in measuring various analytes including metal ions in body fluids such as blood.

It is known to use reference electrodes and measure electromotive force between a reference electrode and an electrode mounted beneath a membrane over which a fluid is passed to determine the ionic content of the fluid. Ions such as potassium, sodium and others are customarily tested in medical laboratories by such equipment. Conventional electronics, pumping and flow meters and the like are interconnected with units for measuring which units contain measuring chambers and electrodes.

SUMMARY OF THE INVENTION

It is an object of this invention to provide a means and method for rapidly and efficiently quantitatively determining ionic concentration of various ions in fluids as for example the blood.

Another object of this invention is to provide a novel and improved testing module unit which can be used with other module units for rapid quantitative measurement with high accuracy of ionic components of extremely small volumes of body fluids in an efficient manner which avoids contamination of the sample to a great extent.

Still another object of this invention is to provide modular units in accordance with the preceding objects which can be stacked seriatim to provide for a plurality of in-line ionic tests to quantitatively determine a plurality of ions in a single sample passed through the units rapidly and efficiently.

Still another object of this invention is to provide means and methods for introduction of calibrating solutions to selected sensing portions of plural modular units rapidly and efficiently without contaminating the calibrating solutions with reference electrode filling solution or other sources of contaminants.

Still another object of this invention is to provide a novel electrode holder and mount for use in a modular unit arrangement in accordance with the present invention which holder provides for membrane mounting and proper positioning and allows exchange of membranes in a rapid and efficient manner.

According to the invention, a testing module unit is dimensioned and arranged to be used with at least one other module unit for testing an analyte in a liquid. The module unit has a body and a narrow diameter through passage. The passageway has an enlarged chamber between ends of the passageway with the chamber being formed on one side of the membrane which membrane is connected to an electrode on its other side through an electrically conductive fluid. The chamber preferably lies substantially in a plane with a first portion of the passageway opening into an inlet of the chamber at an angle to the plane to cause turbulence substantially confined to the opening while permitting smooth flow beyond the opening whereby the chamber acts as a defuser at its entrance and as a nozzle at an exit thereof.

Preferably the chamber is substantially diamond or elliptical in shape and the passageway connecting to the chamber has a diameter of small size so that its cross sectional area along its elongated axis, is essentially equivalent to a diameter of from 0.015 inch to 0.05 inch.

Preferably the electrode membrane has a gel buttressing its inner surface on the side facing the internal reference electrode opposed to the chamber so as to help support the membrane in a substantially planar condition with respect to the module chamber even though there is fluctuating pressure and flow through the module enlarged chamber.

The electrode holder assembly preferably used in conjunction with the testing module unit of the preferred embodiment has an elongated electrode body with a conductive wire having a silver chloride end acting as an internal electrode extending into a compartment which is filled with an electrically conductive liquid and comprising a first chamber of the body. A second chamber compartment preferably comprises a removable cap which is filled with an electrically conductive gel and interconnects primarily with the liquid-filled compartment and interconnects distally with a chemically sensitive ion testing membrane, thereby providing a second chamber filled with a gel of a gelatinous electrically conductive material while the first chamber is filled with an electrically conductive liquid. There is electrical continuity between the internal electrode and the testing membrane. Preferably the gel-filled compartment or second chamber is defined by an electrode cap which is mated and sealed as a part of the holder body and which can be removed for replacement of the membrane if desired.

According to the method of this invention the ionic activity of a fluid such as a body fluid or blood is measured by passing the fluid in a stream between a first measuring or sensing electrode and a second measuring reference electrode. The first measuring or sensing electrode comprises a portion of a sampling chamber. The first measuring or sensing electrode has a membrane and a gel of electrically conductive material underlying the sensor membrane and placed between the membrane and an internal reference electrode surrounded by a conductive fluid. The electromotive force is measured between the first-mentioned measuring sensor electrode and its associated internal reference electrode and the second or last-mentioned measuring reference electrode. The measurement can be carried out during static or flowing conditions of the fluid. In one common embodiment, measurement of two different ionic species is carried out in two chambers of two module units in accordance with this invention while a third module unit houses the associated reference electrode. In an interim between measurements, an auxiliary passageway may be used to flow a calibrating fluid through the measuring chambers to calibrate them without contaminating said calibrating fluid with reference electrode filling solution and at the same time provide means of cleaning all sample pathways and chambers rapidly.

Preferably a modular measuring chamber unit in accordance with this invention is used in conjunction with a second substantially identical unit. More units may be used and locked together by a locking body with electrodes being yieldably positioned against each unit. In one embodiment, one of the module units is a reference electrode carrying unit. This reference electrode unit is of modified design comprising a second passageway permitting cleaning of another adjacent unit without contamination from a modified reference measuring sampling chamber within the unit carrying the auxiliary passageway. In another embodiment the measuring chamber unit is modified only at the reference chamber to make the reference chamber smaller to enhance rapid measurement.

It is a feature of this invention that a plurality of modular units can be mounted seriatim rapidly and efficiently. Because of the hydrodynamic design of the sampling chambers, rapid cleaning can be accomplished. The passageways can be arranged to prevent catching and buildup of debris in the units. The auxiliary passageway when used can provide for rapid and efficient introduction of calibrating fluids away from the sample introduction site and without the need to complicate the sample introduction site with contamination-prone valves. This passageway thus acts as a cleaning passageway in that the chamber to which the calibrating fluid flows is immediately cleaned by the flow and ready to be used for measuring the calibrating fluid.

The use of the gel and particular resilient mounts provide for positive mounting of the sampling chamber in overall arrangements which are highly versatile, rapidly cleaned and easily calibrated and which permit rapid and efficient measurement of ionic concentrations of fluids and particularly body fluids such as blood. Fast response times for tests in the order of under fifteen seconds can be obtained due in part to the small cross section passageways and chambers used.

BRIEF DESCRIPTION OF THE DRAWINGS

The above and other features, objects and advantages of the present invention will be better understood from a reading of the specification in conjunction with the following drawings in which.

DESCRIPTION OF PREFERRED EMBODIMENTS

Figure 1:
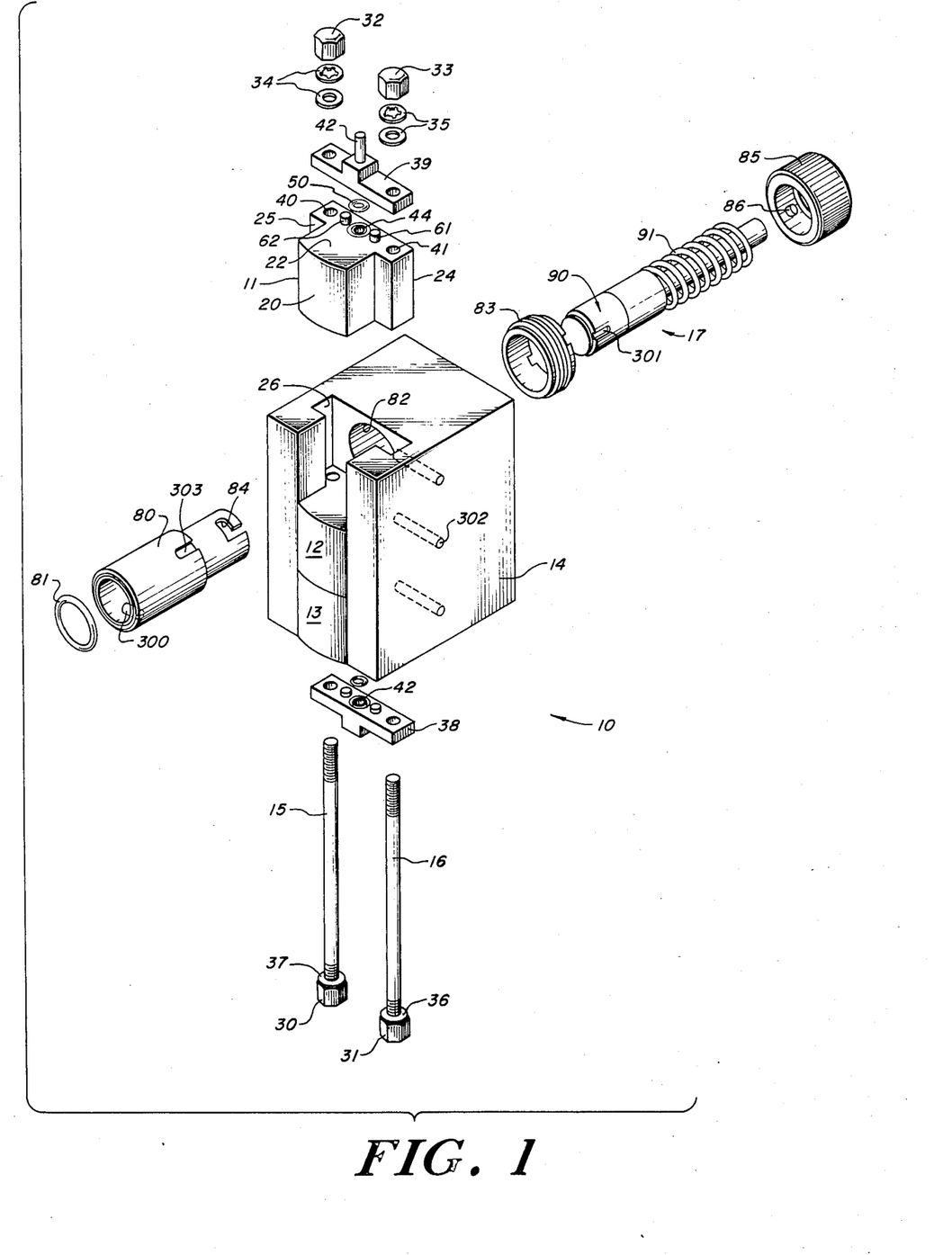
FIG. 1 is an exploded perspective view of a preferred modular unit arrangement of modular sampling chamber units of this invention.

With reference now to the drawings and more particularly FIG. 1, a testing module unit arrangement is shown at 10 in exploded view having three module units 11, 12 and 13 mounted within a housing 14 by locking bolts or rods 15 and 16 with associated locking mechanism and having three electrode mounting assemblies mounted within the housing and illustrated generally at 17, 18 and 19 with 19 being the reference electrode.

Each modular unit of the preferred embodiment 10 is essentially identical to the others used except that unit 11 has a modified chamber 47A of reduced volume to act as a reference electrode sampling chamber and only one modular unit will be fully described for that reason.

Figure 2:
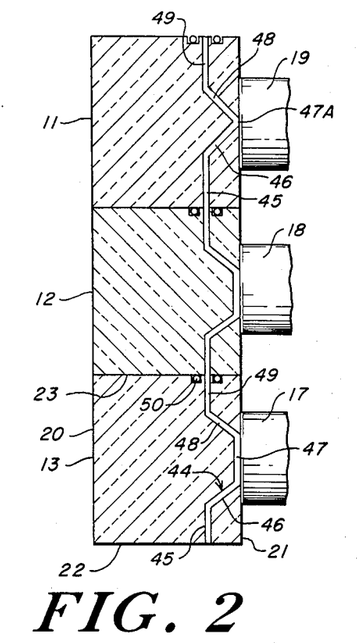
FIG. 2 is a cross-sectional view through the modular measuring chamber units shown in FIG. 1.
Figure 3A:
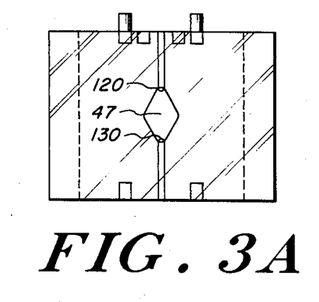
FIG. 3A is a rear view of a single modular measuring unit of the general type shown in FIG. 2.
Figure 3B:
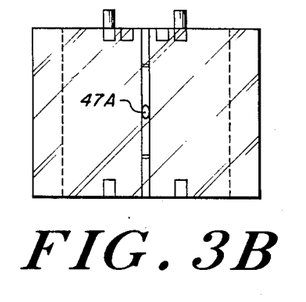
FIG. 3B is a rear view of a single modular measuring unit which is modified at its chamber only to act as a reference measuring or sampling chamber unit.
Figure 3C:
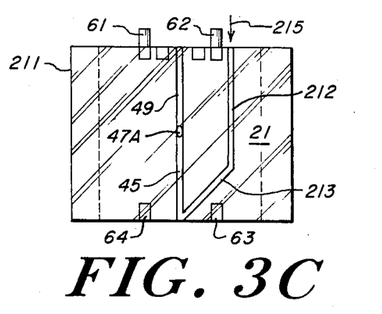
FIG. 3C is a rear view of an alternate embodiment of the modular unit shown at FIG. 3B.

As best shown in FIGS. 1, 2 and 3, each unit has a front face 20, a rear face 21 and generally T-shaped cross section as seen at ends 22 and 23. The T-shaped cross section provides wing-like protrusions or wings 24 and 25 adapted to slide snugly within an undercut T-shaped cutout 26 of a rigid preferably metal housing 14. The T-shaped cutout 26 conforms to the overall cross section of the units 11 so that the units can be slid in seriatim. By dimensioning the housing so as to accommodate the desired plurality of testing module units, one can determine the size desired. In the preferred embodiment, each module unit such as 11 has a height of approximately 1 inch and a front to back depth of about 1 inch. The overall width to the ends of wings 24 and 25 is approximately 1.25 inch. Note that the front wall 20 is curved somewhat for esthetic and viewing magnification purposes although it is considered to be generally parallel to the rear face or wall 21. The particular shape of the front wall 20 can vary as desired as can the cross section so that T or other indented arrangements can be used to provide an undercut for mounting. In some cases other mounting means can be used.

In the preferred embodiments, locking bolts 15 and 16 with nuts 30, 31, 32, 33 and associated washer arrangements 34, 35, 36, 37 are locked to each module unit through end members 38 and 39. Suitable bores 40 and 41 pass completely through each modular unit. The bottom and top end members 38 and 39 are generally T-shaped as shown having an outlet tube 42 and an inlet tube (not shown) on end member 38 providing a through passageway from one end of the assembled units 11, 12 and 13 to the other provided by the passageways noted with the unit passageways 44.

The material of each unit 11, 12 and 13 is preferably a clear plastic having rigidity. Polyethylene, acrylics, vinyl materials and the like as well as other thermoplastic and thermoset materials can be used which provide visibility as well as the needed support. In some cases, glass or other ceramics may be used. The circular through passageway 44 of each block 12 and 13 defines a first passageway portion 45 angled to a second passageway portion 46, a sampling or measuring chamber 47, a third passageway portion 48 and a fourth passageway portion 49. Thus the passageways provide a flow chamber entirely through each unit. The ends of the passageways at the top and bottom parallel surfaces of the block are surrounded by gaskets as shown at 50. Only one gasket need be used on each block since when arranged in modular unit arrangements as shown in FIG. 1, a single gasket will lock to a mating surface of an underlying unit and similarly gasket arrangements can be provided at the through passageway 42 of each end block to provide for fluid sealing. In the unit 11 the chamber 47A has a generally elliptical face adjacent the reference electrode membrane formed by the intersection of passageways 46 and 48.

Each testing module unit further comprises means for aligning and interlinking it with an adjacent unit and/or an end member. This means preferably comprises mating facing surface of adjacent module units and the keying arrangement shown by pins 61, 62. The pins 61, 62 extend from one end of each unit and are adapted to mate with corresponding recesses 63, 64 in adjacent units. Various interlocking arrangements can be used to lock the units together.

In the embodiment shown in FIG. 1, the locking bolts are passed through the end members, the nuts 30, 31, 32, 33 are engaged and assembled with all of the units 11, 12 and 13 lying within the block and locked together.

The interlocked testing module unit is maintained as an integral unit by bolts 15 and 16. The bound together units as shown can be maintained in the housing solely by the pressure exerted by the combination of ferrule 83 and sleeve 80 pressing resilient O-ring 81 against each cuvette.

Figure 4:
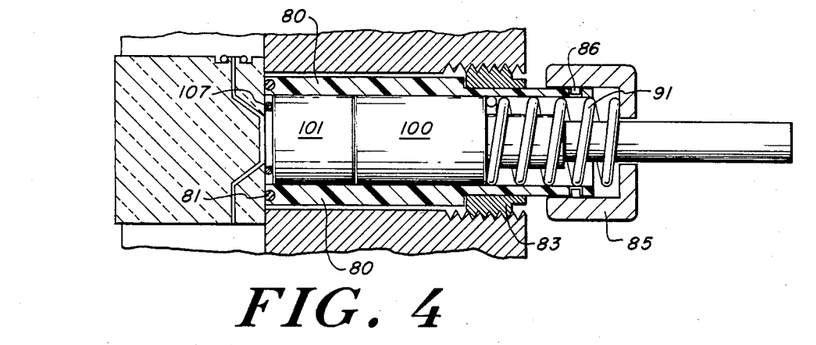
FIG. 4 is a cross-sectional view through a portion of the modular unit arrangement shown in FIG. 1 with the electrode holder shown in full and the surrounding mounting sleeve and mounting assembly shown in cross section.
Figure 5:
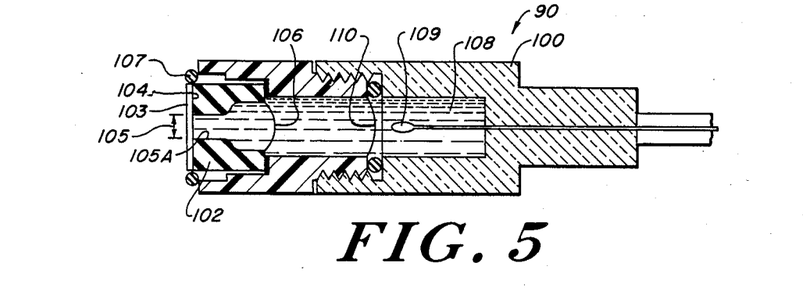
FIG. 5 is a cross section through the electrode holder of FIGS. 1 and 4.

After positioning of units 11, 12 and 13, as best shown in FIGS. 1, 4 and 5, the electrode assemblies are then positioned to form the arrangement of FIGS. 1 and 2. This is done by first positioning a cylindrical stepped electrode holder sleeve 80 having an end O-ring 81 through the housing 14 in a suitable bore provided therein as at 82 and best shown in FIG. 4 to a face 21 of module 11. The cylindrical sleeve 80 is held in place by a locking ferrule 83 which is externally threaded to meet with an internal thread of the housing. There is also an anti-rotation device (pin) 302 mounted in housing 14 and a corresponding slot 303 in the sleeve 80. The sleeve 80 carries an internally extending pin 300 to mate with slot 301 of the holder 90 and prevent turning of holder 90 to prevent rotation when installing the retaining cap.

The cylindrical sleeve carries a bayonet receiver joint L dog 84 as is known. A cap 85 with mating pins 86 are adapted to lock the electrode holder 90 within the housing against the bias of a spring 91. Thus the spring 91 is compressed, the cap engaged with the bayonet dogs and the electrode holder mounting assembly is located as shown in FIG. 4.

The electrode holder assembly itself for a measuring electrode is best shown in FIG. 5.

The holder comprises a main body portion 100 internally threaded to mate with an externally threaded removable membrane or electrode cap 101. The cylindrical electrode cap 101 has bonded to it a cylindrical mount 102 preferably formed of a soft, low durometer or resilient but solid rubber or PVC (plasticized). This material is yieldable but firmly mounts a membrane such as a chemically sensitive membrane of a type generally known in the art for measuring potassium ion concentration or sodium ion concentration or for providing flow of ions for a reference electrode. The mount 102 takes a set but resiliently urges the membrane against surface 21. Valinomycin membranes of the type disclosed in U.S. Pat. No. 3,562,129 are among the membranes that can be used for membrane 103. The membrane 103 is bonded to a flat surface 104 of the mount 102 and has an area 105 defining a portion of a first chamber 106 underlying the membrane. The membrane is preferably substantially planar and preferably does not deviate more than 0.005 from the plane of its outer surface in use to maximize and optimize sealing conditions during measuring and testing of a fluid flowing therepast. In unit 11 the membrane 103 is a reference membrane such as a reference liquid junction membrane.

The cap screws into place and can be removed to change the membrane 103. Thus the cap construction allows ease of membrane replacement. Because locking pins are used to fix and prevent axial rotation of the body 100, the set taken by mount 102 can be positively positioned in original position when the body 100 is removed from the assembly for any reason, thus the seal of the membrane against the surface 21 is preserved.

An O-ring 107 of a rubber material such as a silicone rubber gasket can be used around the membrane to seal it to the side 21 of the module 11 although this would be a secondary seal and is not required in all cases. The O-ring is often dispensed with due to the resilient nature of the mount 102 which acts when pressure is applied to press the membrane against the surface 21 thereby forming a seal between the surface 21 and the mount and enclosing the sampling chamber 47 sealing it against the fluids. Note also that the circular cross-sectional area 105 of the cylindrical bore 105A, is smaller than the cross-sectional area of the sampling chamber 47 so that the entire exposed conductive material cross section under the membrane is exposed to a fluid-filled surface within the chamber.

The chamber 106 is a second chamber of the electrode holder that is aligned with and in fact mates with chamber 108. An internal electrode 109 is electrically conductive to allow external measurement of the signals coming from the electrode sensing surface with an appropriate potentiometric measuring device such as a Keithley Model 616 electrometer.

The electrode holder body 100 can be of a hard vinyl material or other plastic as can the cap portion 101. The preferred mount material having resiliency can be provided by a variety of materials so long as they do not interact with the fluid within the chambers 106 and 108. The cap mount 102 is bonded to membrane 103.

The fluid in chamber 108 is preferably a substantially conventional aqueous conductive fluid of a known type as for example 140 mM NaCl/4 mM KCl.

The chamber 106 is filled with a gel of a conductive material. The gel contacts the liquid and thus there is electrical continuity between the electrode and the membrane allowing electrical sensing of electromotive forces between the internal electrode 109 and a reference electrode adjacent to a second unit in the module.

The gel preferably has a viscosity of at least 15,000 centipoise at 25° C. Materials for the gel are preferably polyacrylamide in an aqueous base with the polyacrylamide being from 3 to 30% by weight of the total gel with a small amount of a cross-linking agent as for example from 2 to 25% by weight of the polyacrylamide. The gel further contains electrically conductive ions as is known in the art for the liquid surrounding the electrode which can be a conventional silver/silver chloride internal electrode. This liquid is conventional internal fill solution and may comprise for example 140 mM NaCl/4 mM KCl.

Preferably the active area 105 underlying the membrane has a cross-sectional area ranging from about 0.00030 square inch to no more than about 0.02 square inch. This minimizes flexure of the membrane as does the use of the gel. The gel has a further function in that it enables a removable tip cap to be positioned adjacent the liquid fill chamber portion with sealing and positive direct contact between the liquid and the gel. It would be difficult to do this if both portions were filled with liquids but simple to have a portion of the gel extend beyond the end of the end cap as best shown at 110 in FIG. 5. The use of a gel also eliminates the risk of a bubble being trapped directly behind the sensing membrane.

Other gels than polyacrylamide can be used and include agar-agar and commercial products such as natrosol a trademarked product of Hercules Chemical Company of Wilmington, Del.

FIG. 3C is an alternate embodiment 211 of a modular unit such as 11 with the only difference being an auxiliary passage 212 as will be described.

FIG. 3A shows the substantially diamond or elliptical shape of the measuring chamber 47. Note that one side of the measuring chamber is actually formed by a side of the membrane 103 or the end of an electrode while an indentation in the body of the testing modular unit forms the other portions of the measuring chamber. The inlet 130 and the outlet 120 provide a defuser and nozzle arrangement respectively. This tends to prevent buildup of particulate matter in the chamber and allows rapid flow. This substantially reduces the "dead space" in the fluid path thus effectively eliminating uncirculating liquid contaminants that typically reside in the dead spaces. The flow path rapidly expands as fluid enters the chamber and is nozzled on the way out by the generally straight sidewalls of the generally diamond-shaped chamber. Preferably there are radii at the junctions of the walls of the chambers to minimize dead flow spaces. Because the chamber passageway portions 46 and 48 either of which can be used as inlets are angled to the substantial plane of the chamber 47 as best shown in FIG. 2, there is some turbulence created which tends to have a cleansing effect but the turbulence effect is localized because of the nozzle and defuser arrangement discussed.

The enlargement toward the center and restriction of the exit are preferred along with straight sidewalls although some variation will permit useful action of the chamber. The chamber wholly encompasses the portion of the membrane which is operatively electrically connected with the internal electrode. Preferably the cross-sectional area of each chamber 47, perpendicular to the direction of flow is less than about ten times the cross-sectional area of the passageway through each unit and the length of each chamber 47 is not less than its width or more than five times its width.

Figure 6:
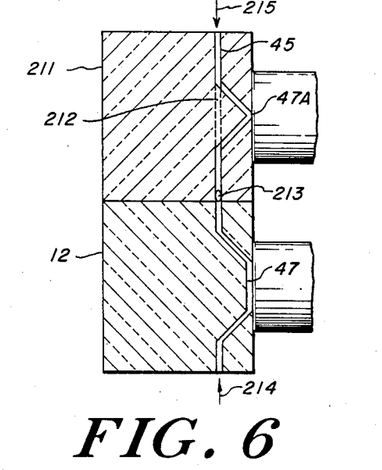
FIG. 6 is a cross section through the alternate embodiment of FIG. 3 in an arrangement of two modular units with one of the modular units being modified in accordance with an alternate embodiment of FIG. 3 of this invention.

Turning now to a modification of a modular unit as shown at 211, all portions of this modular unit 211 are identical to unit 11 as previously described except that an auxiliary passageway 212 is provided in the unit 211. This auxiliary passageway is parallel to the passageway 45 previously discussed and extends to a second portion of the passageway as shown at 213 beyond the first reference sampling chamber 47A but before the second sampling chamber 47 of an adjacent module unit as shown in FIG. 6. Thus when testing body fluids, flow can be established as at arrow 214 and as previously described with the sampling chamber 47A of 211 being opposite a reference electrode and the chamber of 12 being opposite a membrane electrode of the valinomycin type. After testing a blood or other sample, neutral or calibrant solution can be used for cleansing and can be passed through the passageways in the reverse direction as at arrow 215.

With reference now to FIGS. 7–10, a simple testing, cleaning, and calibration series of steps is diagrammatically illustrated. In each of these Figures, blocks such as 211, 12 and 13 are aligned in a modular assembly of the type shown in FIG. 1 in assembled form and are interconnected with suitable fluid conduits, such as 400, 401, 402 having fluid peristaltic pumps 403 and 404 interconnected as shown in lines 401 and 402. A sampling holder for a blood fluid or other sample is shown at 410 with a calibrant supply 411 and a waste or disposal container 412.

In a typical example, a reference electrode is positioned adjacent chamber 47A and forms a part thereof with a measuring electrode adjacent the chamber 47 of block 12 and a second measuring electrode adjacent the chamber 47 of unit 13. The latter two measuring electrodes may for example be valinomycin membranes for measuring potassium, and sodium glass membranes for measuring sodium.

Figure 7:
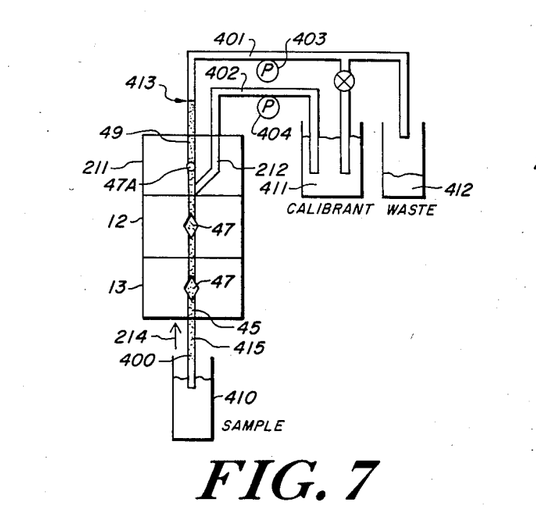
FIGS. 7-10 are semidiagrammatic showings of use of an alternate embodiment of the invention.
Figure 8:
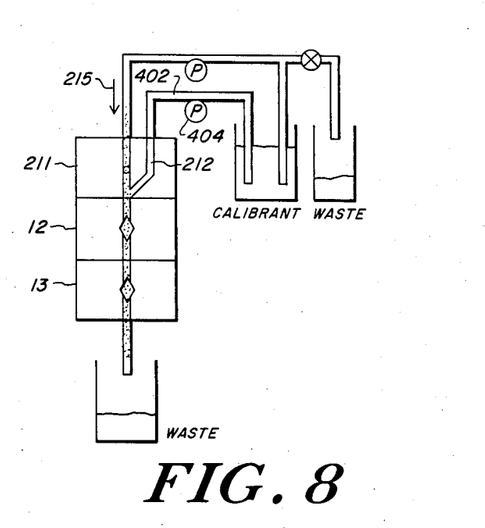

In FIG. 7, a sample fluid is drawn up in the direction of arrow 214 reaching a level of about 413 by activation of pump 403 while pump 404 is stationary. Because pump 404 is stationary, the calibrant in line 402 remains as pure calibrant thus the passageway 212 acts as a stop or valve which is closed to prevent passage of the sample into passageway 212. Thus with 403 activated and pump 404 stationary, the sample 415 is measured as to electric potential between the membrane in chamber 47 of block 13 relative to the membrane of the reference electrode in chamber 47A and simultaneously is measured with respect to the membrane in chamber 47 of block 12 with respect to the reference electrode of chamber 47A. The time period for this measurement is extremely short.

After the first measurement of FIG. 7, flow is reversed by activating pump 403 to cause fluid flow in the direction of arrow 215 from the calibrant chamber 411 until the calibrant washes the chambers 47A, 47, into the waste removing all of the sample. Pump 404 remains stationary so that again there is no flow in line 402 and passageway 212. This is a cleaning step to cleanse all three chambers. However, as the calibrant is flowing past the reference electrode of chamber 47A, it may well pick up unwanted ions from the surface of the reference membrane carrying them through to contaminate chambers 47 of blocks 12 and 13.

Figure 9:
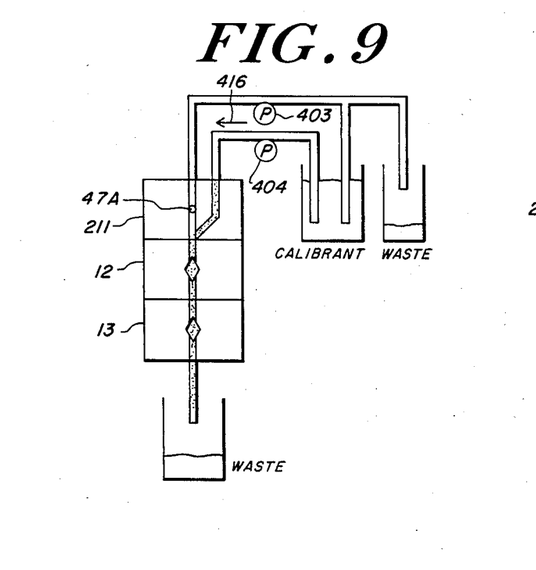

In a third step of FIG. 9, pump 404 is activated to cause flow in the direction of arrow 416 while pump 403 remains stationary blocking flow therepast. Thus calibrant is taken from 411 and flows to wash the chambers 47 of both blocks 12 and 13 without entering the chamber 47A. Thus chambers 47 of blocks 12 and 13 are thoroughly cleansed and prepared for another test cycle.

Figure 10:
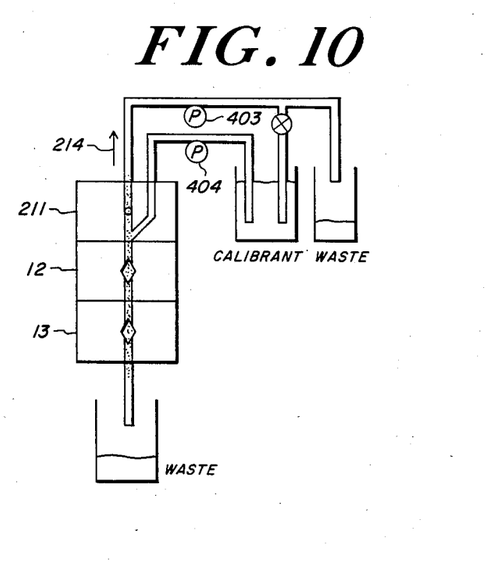

In a next step, shown in FIG. 10, pump 404 is stationary while pump 403 is activated to direct fluid flow upward slightly in the direction of arrow 214 using what is trapped in the line of the fluid shown in FIG. 9 so that clean calibrant lies in each of the three sampling chambers 47A, 47, 47 and an electrical measurement is taken, measuring electrical potential between each of the chambers 47 and the reference chamber 47A.

Thus readings are obtained for calibration of the overall apparatus and for comparison with the readings obtained in FIG. 7.

The process described above can have variations. Thus prior to the calibration step of FIG. 10, the step of FIG. 7 can be repeated after cleaning steps if desired. The calibrant fluid can be replaced with cleaning fluids in steps of FIG. 8. The calibrant itself acts as a cleaning fluid.

The by-pass or auxiliary passageway can provide for extremely rapid cleansing of a system if desired to permit substantially immediate use of a chamber for calibration. The passageway 213 when filled with stationary fluid acts as a unidirectional valve. Of course in some systems the auxiliary passageway need not be used since rapid and continuous flow can be established without the need for an auxiliary passageway feature as now described.

In the method of this invention, the ionic activity of a fluid such as body fluids and blood is determined by passing the fluid in a stream between a first measuring electrode and a second measuring or reference electrode. Thus, as shown in FIG. 2, the flow through the passageway can allow for ionic measurement in a first lower chamber as compared with a reference electrode measurement in a second upper chamber. A third chamber below the lower chamber is provided to allow for testing with still another electrode as to test for another ion. For example, potassium can be tested in one chamber with respect to a reference electrode and sodium in another chamber as known in the art. Because of the modular nature of the units, a plurality of more than three can be used to test for a plurality of ionic concentrations. The chambers can be reversed but in all cases the sample fluid to be tested is flowed or aspirated past the measuring chambers 47 with the reference measuring chamber 47A downstream and last in line.

Although the preferred measuring electrode structure has been shown in FIG. 5, it should be understood that the reference electrode and other electrodes used in a single modular arrangement, can vary somewhat. Thus, in some cases, the reference electrode need not have a membrane mounting but could have other known constructions such as a ceramic frit or open liquid junction and still form portions of the sampling chamber.

In the preferred embodiment, each sampling chamber is formed by a testing or sampling unit or cuvette. At least three are linked together for a dual test having a single reference electrode. The electronics used can be as known in the art as can the preparation of the test samples. Extremely small samples can be tested. Even though the passageways are angularly arranged with respect to the sampling chamber, cleansing is simple and rapid as is testing.

The electrodes used, fill solutions and the like can be as known in the art as for example described in Bailey, P. L., *Analysis with Ion Selective Electrodes*, Hayden, Lond 1976.

In a particular preferred modular arrangement of this invention, the housing 14 has a height of 2.8 inches, a width of 1.75 inches and a depth of 2.28 inches. The block 11 and each block 12 and 13 has a height of 0.93 inches, a front to back dimension of 0.81 inch, a T stem width of 1.25 inch and a flange front to back dimension of 0.31 inch.

Each chamber has a volume of 12 microliters and each passageway has a cross-sectional area that is substantially uniform from one end to the other of 0.0006 square inch. The modules 11, 12 and 13 are formed of acrylic materials. The housing 14 is of metal. The internal reference electrodes used can be silver/silver chloride internal electrodes. Unit 11 contains a dialysis membrane.

The gel behind the valinomycin membrane, when the electrode is a potassium electrode, can be a polyacrylamide 30% aqueous gel with 5% cross-linker added having a viscosity of greater than 15,000 centipoise at 25° C. in unit 12. The fill solution can be 140 mM NaCl/4 mM KCl.

Unit 13 has a membrane electrode construction behind it substantially as described above; however. the membrane can be an alternative PVC membrane for measuring sodium.

While specific embodiments of the present invention have been shown and described, many modifications are possible. In all cases the passageways are designed to enhance speed of operation and to provide clean hydrodynamic flow either through use of the passageway configuration as shown but in some cases with the additional auxiliary passageways.

Various analytes can be tested in apparatus in accordance with this invention. Two channel sodium/potassium analysis is possible as in the preferred embodiment shown in FIG. 1. However, analytes to be tested can include $PO_2$, $PCO_2$, $PNH_3$, chloride, lithium, magnesium, calcium, glucose, urea, lactate, bicarbonate and others as known in the art. The membranes used can vary greatly but are preferably those known in the art as neutral carrier or ion exchange membranes.

The invention's features include reduced sample contamination by the use of the improved cuvette electrode interface, reduction in manufacturing costs due to multiple use of common components for the electrodes and cuvettes. Features further include flat electrode cuvette interfaces with small sample volumes required at high sample visibility with simple maintenance and repair procedures and high speed operation. Fast response can be obtained in the range of about seven and one-half seconds to aspirate a sample through passageway 45 of aligned units and obtain a reading from an electrode and in all cases under a preferred maximum of twenty seconds.

What is claimed is:

1. A testing module unit dimensioned and arranged to be used with at least one other module unit in an arrangement for testing an analyte in a liquid,
    said module unit having a body and a narrow diameter through passageway,
    said passageway having an enlarged chamber intermediate ends of said passageway, said chamber being formed on one side by a membrane of an electrode,
    said chamber lying substatially in a plane with a first portion of said passageway opening into an inlet of said chamber at an angle to said plane to cause turbulence substantially confined to said opening while permitting smooth flow beyond said opening whereby said chamber acts as a defuser at its entrance and as a nozzle at an exit thereof,
    said chamber inlet having an opposed outlet with said chamber varying in cross section from said opening to exit,
    said varying cross section being enlarged toward the center of the chamber and restricted at said exit in a generally diamond shape,
    said passageway having a cross-sectional area corresponding to a diameter of from 0.015 inch to 0.05 inch,
    said chamber having a maximum cross-sectional area less than ten times the cross-sectional area of said passageway.

2. A testing module unit in accordance with claim 1 and further comprising said chamber defining an area greater than an area defined by said membrane whereby said membrane is wholly encompassed by said chamber.

3. An electrode holder for use in a testing module unit,
said electrode holder comprising an elongated electrode body having a source of electricity connected therethrough to an internal electrode lying within a first chamber therein,
said first chamber being elongated and open to a second chamber underlying a chemically sensitive ion testing membrane,
said second chamber being filled with a gelatinous electrically conductive material and said first chamber being filled with an electrically conductive liquid whereby there is electrical continuity between said internal electrode and said testing membrane.

4. An electrode holder in accordance with claim 3 wherein said second chamber is defined by a second electrode body portion adapted to be mated with said first body portion in sealing engagement therewith to positively bring said gel into contact with said liquid.

5. An electrode holder in accordance with claim 4 wherein said second body portion is in the form of a removable cap having an end surface at which extends said gel.

6. An electrode holder in accordance with claim 3 and further comprising a soft resilient yieldable mount for said membrane defining a planar surface to which said membrane is attached and maintained in substantially planar form,
said mount being adapted to be resiliently compressed to seal said membrane against a cuvette overlying said membrane whereby a sealed chamber can be defined in part by said membrane and said cuvette.

7. An electrode holder in accordance with claim 3 wherein said gel underlies said flexible membrane at an area of said membrane ranging from about 0.0003 square inches to 0.02 square inch.

8. A method of determining the ionic activity of a fluid by passing said fluid in a stream between a first measuring electrode and a second measuring reference electrode,
said first measuring electrode comprising a portion of a sampling chamber, said first measuring electrode having a membrane with a gel of electrically conductive material underlying the membrane and interspersed between it and an internal electrode portion surrounded by a conductive fluid,
and measuring the electromotive force between said reference electrode and said measuring electrode.

9. A method in accordance with the method of claim 8 and further comprising said fluid being in a flowing condition and continuously monitoring said electromotive force.

10. A method in accordance with the method of claim 8 wherein said fluid is static during said measuring.

11. A method in accordance with the method of claim 8 wherein said gel has a viscosity greater than 15,000 centipoise at 25° C.

12. A method in accordance with the method of claim 8 further comprising said chamber defining a volume greater than passageways leading to and from said chamber with said passageways leading to and from said chamber defining an overall cross section equivalent to a diameter in the range of from 0.015 inch to 0.05 inch.

13. A method in accordance with the method of claim 12 and further comprising said fluid flow in said passageways being directed at angles to said chamber whereby localized turbulence is created at exit of passageway to cleanse said chamber with said chamber acting first as a defuser and second as a nozzle for said fluid in passing through said chamber,
said chamber having a cross section not exceeding ten times the said cross section of said passageways.

14. method in accordance with the method of claim 12 and further comprising said first measuring electrode being in a first test modular unit and said measuring electrode being in a second test modular unit with said passageway extending through said units to permit flow of sample fluid therethrough.

15. A method in accordance with claim 14 and further including a third test modular unit aligned with said first and second units carrying a third measuring electrode to permit measuring another ionic acitivity in said last-mentioned unit.

16. A first testing module unit dimensioned and arranged to be used with at least one other identical module unit in an arrangement for testing an analyte in a liquid,
said module unit having a body, a rear face and a narrow diameter though passageway,
said passageway having an enlarged chamber intermediate ends of the passageway, said chamber being formed on one side by a membrane of an electrode,
said chamber lying substantially in a plane with a first portion of the passageway opened into an inlet of the chamber at an angle to the plane to cause turbulence substantially confined to said opening while permitting smooth flow beyond said opening whereby said chamber acts as a defuser at its entrance and a nozzle at an exit thereof,
said membrane being mounted on an electrode holder,
said electrode holder resiliently urged toward said chamber side,
a second testing modular unit aligned end to end with said first-mentioned modular unit, said second unit having a through passageway mating with said first-mentioned passageway,
said first and second-mentioned units each having outwardly extending side wings and a rear face,
said side wings being mounted seriatim in a housing,
said housing defining a first and second bore passing therethrough and lying adjacent a rear face of said first and second testing modular units respectively,
at least one bore carrying an electrode holder,
said electrode holder being maintained in place by a screw threaded ferrule compressing a sleeve through an O-ring seal engaging a rear face of a unit,
an electrode body of said holder being mounted on said sleeve by a resilient spring engaged by an end cap mounted on said sleeve.

17. A method of cleaning and calibrating a first sampling measuring chamber contained in a modular measuring chamber unit which unit is positioned adjacent a second modular unit containing a reference electrode second chamber,
wherein said units define a passageway between said chambers and through said units,
a second one-way valve passageway intersecting said passageway between said reference electrode second chamber and said sampling measuring chamber, said method comprising passing a liquid sample through said passageway from said sampling measuring chamber to said reference chamber whereby a measurement of electrical potential can be taken between said chambers while maintaining said second passageway filled with a second fluid other than said sample, reversing fluid flow between said reference chamber and sampling measuring chamber by passing a cleaning fluid from said reference chamber through said sampling measuring chamber to remove the sample fluid while maintaining said second passageway filled with a fluid, passing a cleansing fluid flow through said secondary passageway to said sampling measuring chamber without said last-mentioned flow first passing to said reference chamber, and reversing flow again to pass a calibrant fluid from said sampling chamber to said reference chamber while said secondary passageway maintains a stationary fluid whereby a calibration measurement can be made to measure electrical potential between said sampling chamber and said reference chamber.

18. A method in accordance with the method of claim 17 and further comprising all fluid flow other than the sample fluid flow being of a calibrating liquid.

19. A method in accordance with the method of claim 17 wherein said first-mentioned reversing step is carried out while maintaining said second passageway filled with a stationary fluid.

* * * * *